United States Patent [19]

Fisher et al.

[11] Patent Number: 5,100,912
[45] Date of Patent: Mar. 31, 1992

[54] BIS(BENZYLPYRROLIDINE) DERIVATIVES AS DOPAMINE AGONISTS

[75] Inventors: Lawrence E. Fisher, Mountain View; Joseph M. Muchowski, Sunnyvale, both of Calif.; Edvige Galeazzi, Mexico City, Mexico; Roberto P. Rosenkranz, Menlo Park; Deborah L. McClelland, Palo Alto, both of Calif.

[73] Assignee: Syntex (U.S.A.) Inc., Palo Alto, Calif.

[21] Appl. No.: 631,524

[22] Filed: Dec. 21, 1990

Related U.S. Application Data

[63] Continuation-in-part of Ser. No. 523,293, May 14, 1990, abandoned, which is a continuation-in-part of Ser. No. 369,366, Jun. 21, 1989, abandoned.

[51] Int. Cl.$^5$ .................... A61K 31/40; C07D 207/06
[52] U.S. Cl. .................... 514/422; 548/523; 548/524
[58] Field of Search ................. 548/524, 523; 514/422

[56] References Cited

U.S. PATENT DOCUMENTS

| | | | |
|---|---|---|---|
| 2,708,207 | 5/1955 | Girod | 260/567.6 |
| 2,777,858 | 1/1957 | Girod et al. | 260/313 |
| 4,221,788 | 9/1980 | Eistetter | 424/244 |
| 4,279,918 | 7/1981 | Eistetter et al. | 514/408 |
| 4,613,606 | 9/1986 | Clark et al. | 514/307 |

FOREIGN PATENT DOCUMENTS 0294973 12/1988 European Pat. Off. .

OTHER PUBLICATIONS

J. E. Nordlander et al., J. Org. Chem. 1984, 49(22), 4107–4111 "Friedel–Crafts Acylation . . .".

E. Elamin et al., Int. J. Appl. Radiat. Isat. 1985, 36(4), 269–73 "Preparation of C-Labelled Raclopride . . .".
A. N. Brubaker et al., J. Med. Chem. 1986, 29(8), 1528–1531 "Synthesis and Pharmacological Evaluation . . .".
L. Florvall et al., J. Med. Chem. 1982, 25(11), 1280–1286. "Potential Neurolephic Agents . . ."
Western Pharmacology Socitey 1990 Meeting Programme. Programme 2/26/90, Abstract 6 and 7.

*Primary Examiner*—John M. Ford
*Assistant Examiner*—Jyothsna Venkat
*Attorney, Agent, or Firm*—Derek P. Freyberg

[57] ABSTRACT

Compound of Formula I

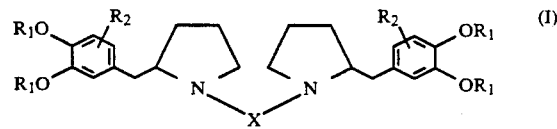

in which:
$R_1$ is hydrogen, lower alkyl, —C(O)$R_3$, or —C(O)N$R_3R_4$, where $R_3$ and $R_4$ are independently lower alkyl, phenyl, or phenyl lower alkyl;
$R_2$ is hydrogen or lower alkyl; and
X is —(CH$_2$)$_m$— where m is an integer of 1 to 10, or —(CH$_2$)$_n$Y(CH$_2$)$_n$—where n is an integer of 1 to 3 and Y is oxygen or sulfur, their individual R,R—; R,S—; and S,S-stereoisomers, and racemic or non-racemic mixtures of stereoisomers, and their pharmaceutically acceptable salts are dopamine agonist compounds useful in the treatment of hypertension and congestive heart failure in mammals.

15 Claims, No Drawings

BIS(BENZYLPYRROLIDINE) DERIVATIVES AS DOPAMINE AGONISTS

CROSS-REFERENCE TO RELATED APPLICATIONS

This application is a continuation-in-part of our copending application, Ser. No. 07/523,293, filed May 14, 1990, now abandoned; which is a continuation of our application Ser. No. 07/369,366, filed June 21, 1989, now abandoned. The disclosure of Ser. No. 07/523,293, and of other documents referred to throughout this application are incorporated herein by reference.

BACKGROUND OF THE INVENTION

1. Field of the Invention

The invention relates generally to dopamine agonists and more particularly to bis(benzylpyrrolidine) derivatives which are orally active dopamine agonists.

2. Description of Prior Art

Dopamine, 4-(2-aminoethyl)-1,2-benzenediol, is a marketed sympathomimetic with significant dopaminergic actions in the periphery. Drugs having the pharmacological effect of dopamine are referred to as dopaminergic agonists; some sympathomimetics appear to act on dopamine receptors in the central nervous system. In the periphery, dopamine receptors are prominent in the splanchnic and renal vascular beds, where they mediate vasodilatation. Dilatation in these beds is important in the treatment of shock and congestive heart failure, since these beds are often critically constricted in these conditions. Dopamine is used in the management of these disorders. It may also be used to induce diuresis, probably consequent to renal vasodilation, at least in part.

Dopamine is a natural catecholamine formed by the decarboxylation of 3,4-dihydroxyphenylalanine (DOPA). It is a precursor to norepinephrine in noradrenergic nerves and is also a neurotransmitter in certain areas of the central nervous system, especially in the nigrostriatal tract, and in a few peripheral sympathetic nerves.

In the central nervous system and the mesenteric, coronary and renal vascular beds, it acts upon dopamine receptors that are distinct from $\alpha$- and $\beta$-adrenoreceptors. At these dopamine receptors, haloperidol is an antagonist. In the above-named vascular beds it causes vasodilatation. The renal vasodilatation may be one stimulus for diuresis. Dopamine also has moderate $\beta_1$- and weak $\alpha$-agonist activities, part of which is attributable to norepinephrine released by dopamine. During a low rate of intravenous infusion, only vasodilatation in the mesenteric, coronary and renal vascular beds usually predominates, and hypotension sometimes occurs. At an intermediate rate of infusion, the heart rate and force of contraction are increased, as is cardiac output, and blood pressure may increase accordingly. At high rates of infusion, $\alpha$-adrenergic vasoconstriction in the mesenteric, coronary and renal vascular beds may overcome the dopaminergic vasodilatation in some recipients.

Dopamine is used in the treatment of shock, for which it has several advantages. Firstly, vasodilatation can often be effected in the two organs most likely to suffer ischemic damage in shock (kidney and small bowel); blood may be moved from the skeletal muscle to more vital organs, cardiac stimulation improves a usually deteriorated cardiac function, and diuresis also helps to preserve renal function. Although dopamine is now the vasopressor agent of choice in shock, a substantial fraction of cases nevertheless fail to respond. Dopamine is also used to treat acute heart failure; the decreased vascular resistance decreases the cardiac afterload, the cardiostimulatory actions improve cardiac output, and the diuresis lessens edema.

U.S. Pat. No. 4,613,606, issued Sept. 23, 1986, discloses a number of tetrahydroisoquinoline derivatives which are indicated as being calcium channel blockers and as such useful for the treatment of cardiovascular disorders including angina, hypertension and congestive heart failure.

European Patent Application No. 0 294 973, published Dec. 14, 1988, discloses a number of dopamine $\beta$-hydroxylase (DBH) inhibitors. Dopamine is hydroxylated to norepinephrine by DBH in the presence of oxygen and ascorbic acid; and DBH inhibitors are believed to be effective in treating hypertension.

SUMMARY OF THE INVENTION

In a first aspect, this invention provides compounds of Formula I

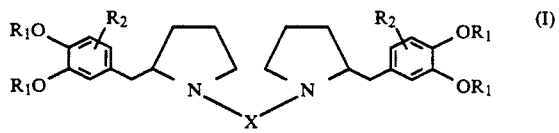

in which:

$R_1$ is hydrogen, —C(O)R$_3$, or —C(O)NR$_3$R$_4$, where R$_3$ and R$_4$ are independently lower alkyl, phenyl, or phenyl lower alkyl;

$R_2$ is hydrogen or lower alkyl; and

X is —(CH$_2$)$_m$— where m is an integer of 1 to 10, or —(CH$_2$)$_n$Y(CH$_2$)$_n$— where n is an integer of 1 to 3 and Y is oxygen or sulfur, their individual R,R-; R,S-; and S,S-stereoisomers, and racemic or non-racemic mixtures of stereoisomers, and their pharmaceutically acceptable salts.

In a second aspect, this invention provides pharmaceutical compositions and dosage forms containing a of Formula I as described in the preceding paragraph (as an individual stereoisomer or mixture of stereoisomers, or as a pharmaceutically acceptable salt of the individual stereoisomer or mixture of stereoisomers) with a pharmaceutically acceptable carrier.

In a third aspect, this invention provides methods of treating hypertension, congestive heart failure and acute renal failure in mammals by administration of a compound of Formula I as described in the preceding paragraph (as an individual stereoisomer or mixture of stereoisomers, or as a pharmaceutically acceptable salt of the individual stereoisomer or mixture of stereoisomers), or a pharmaceutical composition or dosage form containing it.

In a fourth aspect, this invention provides compounds of Formula I

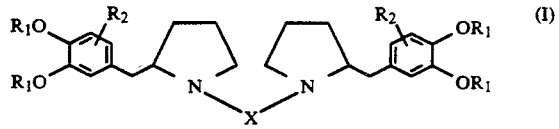

in which:

$R_1$ is lower alkyl;

$R_2$ is hydrogen or lower alkyl; and

X is —(CH$_2$)$_m$— where m is an integer of 1 to 10, or —(CH$_2$)$_n$Y(CH$_2$)$_n$— where n is an integer of 1 to 3 and Y is oxygen or sulfur, their individual R,R—; R,S—; and S,S-stereoisomers, and racemic or non-racemic mixtures of stereoisomers, and their pharmaceutically acceptable salts, which are useful as intermediates in the preparation of compounds of Formula I in which $R_1$ is hydrogen, —C(O)R$_3$, or —C(O)NR$_3$R$_4$, where R$_3$ and R$_4$ are independently lower alkyl, phenyl, or phenyl lower alkyl; as described above.

In a fifth aspect, this invention provides methods of preparing compounds of Formula I in which $R_1$ is hydrogen, —C(O)R$_3$, or —C(O)NR$_3$R$_4$, where R$_3$ and R$_4$ are independently lower alkyl, phenyl, or phenyl lower alkyl; and their pharmaceutically acceptable salts, which comprises:

a) reacting a compound of Formula I wherein $R_1$ is lower alkyl, preferably methyl, with a deprotecting agent to afford a compound of Formula I wherein $R_1$ is hydrogen; optionally followed by b) converting a compound of Formula I to a pharmaceutically acceptable salt of Formula I; or c) converting a pharmaceutically acceptable salt of Formula I to a free compound of Formula I; or d) converting a pharmaceutically acceptable salt of Formula I to another pharmaceutically acceptable salt of Formula I; or e) converting a compound of Formula I to an ester of Formula I.

DETAILED DESCRIPTION OF THE INVENTION

Definitions

"Alkyl" means a branched or unbranched saturated hydrocarbon chain containing 1 to 10 carbon atoms, such as methyl, ethyl, propyl, iso-propyl, butyl, iso-butyl, tert-butyl, n-pentyl, n-hexyl, 2-methylheptyl, n-octyl and the like, unless otherwise indicated.

"Lower alkyl" means a branched or unbranched saturated hydrocarbon chain containing 1 to 4 carbon atoms, such as methyl, ethyl, propyl, isopropyl, tert-butyl, butyl, iso-butyl and the like, unless otherwise indicated.

"Lower alkoxy" means the group -OR wherein R is lower alkyl as herein defined.

"Halo" means fluoro, chloro, bromo, or iodo, unless otherwise indicated.

"Phenyl" includes all possible isomeric phenyl radicals, optionally monosubstituted or disubstituted with substituents selected from the group consisting of lower alkyl, lower alkoxy, hydroxy, trifluoromethyl and halo.

"Phenyl lower alkyl" means phenyl as defined herein attached to a lower alkyl group as defined herein.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and substituted phenyl.

"Protecting group" means any suitable chemical group that is commonly used in the practice of organic chemistry to modify one or more of the major functional groups in a molecule for the purpose of selectively performing a chemical reaction at another reactive site in a multifunctional molecule. A protecting group is typically formed in a selective manner and is stable to subsequent reactions on the molecule and is selectively removed by reagents that do not attack the regenerated functional group. Suitable protecting groups for the amino group are alkyl carbamates, such as methyl carbamate and substituted methyl carbamates such as cyclopropylmethyl, diisopropylmethyl, 9-fluorenylmethyl carbamates, and the like, ethyl carbamate and substituted ethyl carbamates such as 2,2,2-trichloroethyl, 2-haloethyl, and the like, propyl and isopropyl carbamates and substituted propyl and isopropyl carbamates such as 1,1-dimethylpropyl, 1-methyl-1-phenylethyl and derivatives, isobutyl, t-butyl carbamate, t-amyl carbamate, vinyl and allyl carbamate, phenyl and substituted phenyl carbamates, benzyl carbamate and derivatives such as p-methoxybenzyl, 3,5-dimethoxybenzyl, o- and p-nitrobenzyl, halobenzyl, and the like; amides and their derivatives such as N-acetyl and derivatives like N-dichloroacetyl, N-trifluoroacetyl, and the like, substituted N-propionyl derivatives such as N-3-phenylpropionyl and derivatives, N-o-nitrocinnamoyl and the like, cyclic imide derivatives such as N-phthaloyl, N-2,3-diphenylmaleoyl, and the like.

A "leaving group" means a group capable of being displaced by a nucleophile in a chemical reaction, for example chloro, bromo, iodo, (alkyl or aryl)sulfonate ester, (alkyl or aryl)sulfinate ester, (alkyl or aryl)-carbamate, and the like.

The term "pharmaceutically acceptable salts" refers to salts of the subject compounds which possess the desired pharmacological activity and which are neither biologically nor otherwise undesirable. These salts are formed with inorganic acids such as hydrochloric acid, hydrobromic acid, sulfuric acid, nitric acid or phosphoric acid; or organic acids such as acetic acid, propionic acid, glycolic acid, pyruvic acid, malonic acid, succinic acid, malic acid, maleic acid, fumaric acid, tartaric acid, citric acid, benzoic acid, ethanesulfonic aicd, p-toluenesulfonic acid and the like.

"Esters" are those compounds of Formula I in which $R_1$ is —C(O)R$_3$ or —C(O)NR$_3$R$_4$, where R$_3$ and R$_4$ are independently lower alkyl, phenyl, or phenyl lower alkyl.

The compounds of this invention possess asymmetric centers and thus can be produced as mixtures of stereoisomers or as individual stereoisomers. The individual stereoisomers may be obtained by using an optically active starting material, by resolving a racemic or non-racemic mixture of an intermediate at some appropriate stage of the synthesis, or by resolution of the compound of formula (I). It is understood that the individual stereoisomers as well as mixtures (racemic and non-racemic) of stereoisomers are encompassed by the scope of the present invention. The compounds of this invention possess at least two asymmetric centers and thus can be produced as mixtures of stereoisomers or as individual R,R—; S,S—; or R,S-stereoisomers. The individual enantiomers may be obtained by resolving a racemic or non-racemic mixture of an intermediate at some appropriate stage of the synthesis. It is understood that the individual R,R—; S,S—; and R,S-stereoisomers as well as mixtures of stereoisomers are encompassed by this invention. The R,R-stereoisomer is most preferred due to its greater activity, especially when administered orally.

"Isomers' are different compounds that have the same molecular formula.

"Stereoisomers" are isomers that differ only in the way the atoms are arranged in space.

"Enantiomers" are a pair of stereoisomers that are non-superimposable mirror images of each other.

"Diastereoisomers" are stereoisomers which are not mirror-images of each other.

"Epimers" are diastereoisomers which differ only in the configuration of one asymmetric center.

"Meso" isomers are diastereoisomers that are optically inactive by reason of internal compensation. Compounds of formula (I) where one of the two asymmetric carbon atoms is R and the other is S are meso compounds, because equal and opposite optical rotations are thus produced.

"Racemic mixture" means a mixture containing equal parts of individual enantiomers. "Non-racemic mixture" is a mixture containing unequal parts of individual enantiomers or stereoisomers.

The term "treatment" as used herein covers any treatment of a disease and/or condition in a mammal, particularly a human, and includes:

(i) preventing a disease and/or condition from occurring in a subject which may be predisposed to the disease and/or condition but has not yet been diagnosed as having it;

(ii) inhibiting the disease and/or condition, i.e., arresting its development; or (iii) relieving the disease and/or condition, i.e., causing regression of the disease and/or condition.

The system used in naming the intermediates and product compounds of the present invention is shown below, using a compound of formula (I) as an example.

A racemic compound of formula (I) wherein each $R_1$ and $R_2$ is hydrogen and X is $-(CH_2)_7-$ is named:

($\pm$)-1,7-bis[2-(3,4-dihydroxybenzyl)pyrrolidin-1-yl]-heptane.

A racemic compound of formula (I) wherein each $R_1$ and $R_2$ is hydrogen and X is $-(CH_2)_2O(CH_2)_2-$ is named:

($\pm$)-1,5-bis[2-(3,4-dihydroxybenzyl)pyrrolidin-1-yl]-3-oxapentane.

A racemic compound of formula (I) wherein each $R_1$ is $-C(O)CH_3$, each $R_2$ is 5-methyl, and X is $-(CH_2)_4-$ is named:

($\pm$)-1,4-bis[2-(3,4-diacetoxy-5-methylbenzyl)pyrrolidin-1-yl]butane.

As used in this specification and the appended claims, the singular forms "a", "an" and "the" include plural reference unless the context clearly dictates otherwise. Thus, for example, reference to a bis(benzylpyrrolidine) derivative includes mixtures of such compounds, reference to "the hydrogenating reaction" includes reference to a plurality of hydrogenating reactions, reference to "an ester" includes mixtures of esters and so forth.

Methods of Preparation

One method of preparing racemic compounds of formula (I) is illustrated below in Reaction Scheme I.

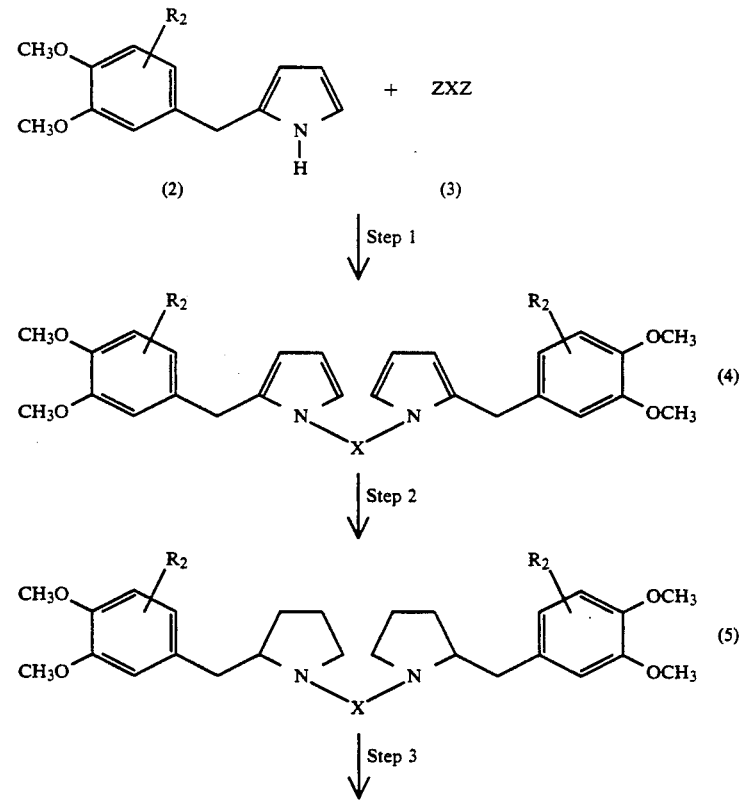

REACTION SCHEME I

REACTION SCHEME I

-continued

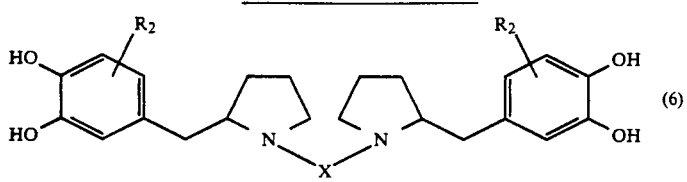

In Reaction Scheme I, $R_2$ and X are as defined in the Summary of the Invention. $R_2$ is preferably hydrogen; and X is preferably $-(CH_2)_m-$ where m is an integer of 4 to 8, more preferably 6. Each Z is a leaving group, preferably bromine. The compounds of Formula 6 thus prepared are compounds of Formula I in which each $R_1$ is hydrogen.

No stereoisomerism is indicated throughout Reaction Scheme I. However, asymmetric centers at C-2 of each pyrrolidine ring are introduced in Step 2 by reduction of the pyrrole rings, and are found in compounds of Formulas 5 and 6.

Step 1

The preferred method of preparing the compounds of Formula I as a racemic mixture starts from the compound of Formula 2, an optionally substituted 2-(3,4-dimethoxybenzyl)pyrrole. These compounds can be prepared by methods known to those of ordinary skill in the art. Thus, for example, 2-(3,4-dimethoxybenzyl)pyrrole may be prepared by the sodium borohydride reduction of 2-(3,4-dimethoxybenzoyl)pyrrole, as described by Greenhouse et. al., *J. Org. Chem.*, 50, 2961 (1985). The synthesis of the 2-(3,4-dimethoxybenzoyl)pyrrole is also described in the Greenhouse et al. article, which is incorporated herein by reference to disclose the synthesis of such compounds and the compound (2).

Typically, 2-(3,4-dimethoxybenzyl)pyrrole is dissolved in a polar solvent such as dimethylsulfoxide, sulfolane and the like, preferably dimethylformamide. The solution is added to a suspension of 1 to 2 molar equivalents, preferably about 1.2 molar equivalents, of a metal hydride such as potassium hydride, lithium hydride, preferably sodium hydride, preferably in the same polar solvent. The reaction is carried out at a temperature of about 0°-30° C., preferably about 25° C., for about 30 minutes to 6 hours, preferably about 2 hours. To this reaction mixture is then added ZXZ, the compound of Formula 3, preferably 1,6-dibromohexane. The reaction is carried out at a temperature in the range of about 0°-30° C., preferably about 25° C., for about 1 to 8 hours, preferably about 3 hours. When the reaction is substantially complete, the bis(benzylpyrrole) product of Formula 4 is isolated and purified by conventional means, preferably chromatography.

Step 2

In Step 2, the bis(benzylpyrrole) of Formula 4 is reduced to the corresponding bis(benzylpyrrolidine) of Formula 5. Typically, compound (4) is dissolved in an organic acid solvent, preferably acetic acid, and a hydrogenation catalyst added, preferably 5% rhodium on alumina. The mixture is reacted with hydrogen at about 20-80 p.s.i., preferably about 45 p.s.i., at a temperature of about 0°-30° C., preferably about 25° C., until about the theoretical amount of hydrogen is absorbed. When the reaction is substantially complete, the bis(benzylpyrrolidine) product of Formula 5 is isolated by conventional means, preferably chromatography.

Step 3

In Step 3, the methyl protecting groups of the compound of Formula 5 are removed, using a deprotecting agent such as $BBr_3$. Typically, a solution of compound 5 in a polar solvent such as dichloromethane is cooled to $-70°$ C. under an inert atmosphere, and $BBr_3$ is added. The mixture is warmed to room temperature, and excess $BBr_3$ and solvents are removed in vacuo to give compound 6, a compound of Formula I in which each $R_1$ is hydrogen.

Compounds of Formula I prepared using the processes of Reaction Scheme I may be resolved into individual stereoisomers. Techniques for resolution are well-known to the art of pharmaceutical organic synthesis; and those of ordinary skill in the art will have no difficulty, having regard to their knowledge and this disclosure, in performing such resolutions. However, the preferred method of obtaining individual stereoisomers of the compounds of Formula I is by stereoselective synthesis, as discussed further below.

A convenient method of directly preparing the optically active isomers of compounds of Formula I is shown in Reaction Scheme II below.

REACTION SCHEME II

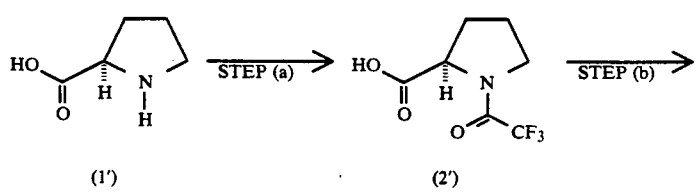

REACTION SCHEME II -continued
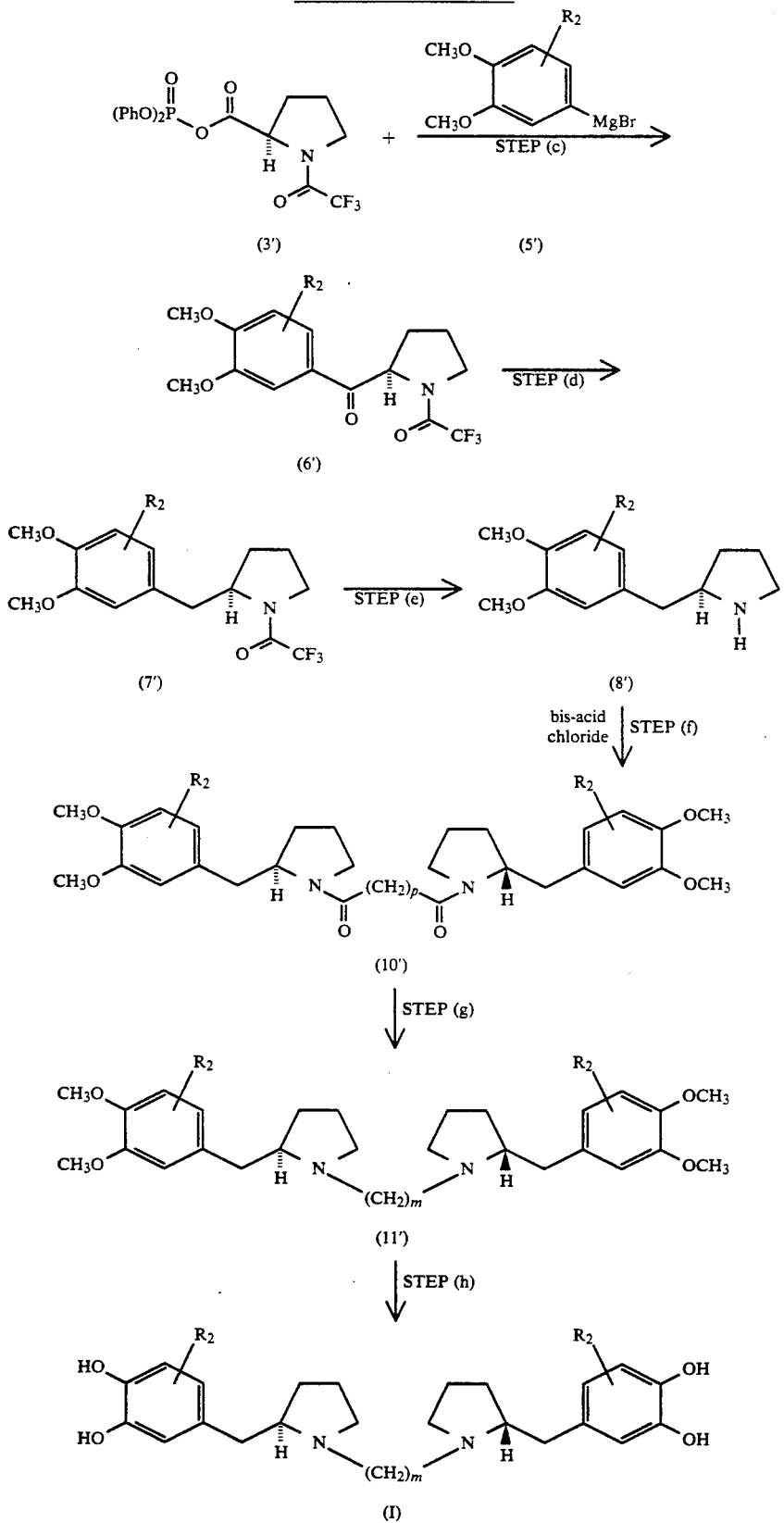
In Reaction Scheme II, $R_2$ is as defined in the Summary of the Invention, preferably hydrogen, and the reaction scheme will be described below for the case where $R_2$ is hydrogen; and p is m-2, where m is an integer of 2 to 10, preferably 4 to 8, more preferably 6.

The compounds thus prepared are compounds of Formula I in which each $R_1$ is hydrogen. Preparation of only the R,R-stereoisomer is shown throughout Reaction Scheme II. It will be apparent, however, that:

(1) compounds where $R_2$ is other than hydrogen may also be prepared, by the use of an appropriate Grignard reagent (5');

(2) compounds where X is —$(CH_2)_nY(CH_2)_n$— may also be prepared, by the use of a bis(acid chloride) of the formula $ClC(O)(CH_2)_{n-1}Y(CH_2)_{n-1}C(O)Cl$; and (3) the S,S-stereoisomer, or mixtures of isomers, may be prepared, by the use of (S)-proline or mixtures of (R)- and (S)-proline.

Step (a)

Step (a) involves the protection of the amine function of the proline with an amine protecting group as defined earlier, preferably as the trifluoroacetyl derivative. Typically, the amine (1') is reacted, in an inert solvent such as benzene, toluene, acetonitrile, diethyl ether, chloroform, methylene chloride or, preferably, tetrahydrofuran, with from 1-5 molar equivalents, preferably about 2 molar equivalents, of a trifluoroacetylating agent, preferably ethyl trifluoroacetate, in the presence of about 1-3 molar equivalents, preferably about 1.5 molar equivalents, of a tertiary organic base, such as pyridine, N-methylpiperidine, 4-dimethylaminopyridine and the like, preferably 1,1,3,3-tetramethylguanidine. The reaction is carried out at a temperature of about 0°-40° C., preferably about 25° C., for about 10 minutes to 4 hours, preferably about 30 minutes. When the reaction is substantially complete, the (R)-1-trifluoroacetylproline (2') is isolated by conventional means.

Step (b)

In Step (b), the carboxyl group of the protected proline (2') is converted to a derivative which on reaction with an organometallic compound gives a ketone. Methods for converting carboxyl groups to ketones are well known in the art, and include converting the carboxyl group to an acid halide and reacting this with a lithium dialkylcopper reagent or an organocadmium reagent, or converting the carboxyl group to a teritary amide and reacting this with a Grignard reagent or organolithium derivative. Such reactions are discussed in more detail in *Advanced Organic Chemistry* by March, for example on pages 439–440 (2nd Edition), the pertinent portions of which are incorporated herein by reference. The preferred method is to convert the carboxyl group to a mixed anhydride with diphenylphosphoric acid. Typically, the protected proline (2') is dissolved in an inert solvent as defined above, preferably methylene chloride, and reacted with from 0.5-1.5 molar equivalents, preferably about 1 molar equivalent, of an organochlorophosphate, preferably diphenyl chlorophosphate, in the presence of about 1-3 molar equivalents, preferably about 1.5 molar equivalents, of a tertiary organic base, such as pyridine, N-methylpiperidine and the like, preferably N-methylmorpholine. The reaction is carried out at a temperature of about −20° C. to 20° C., preferably about 0° C., for about 5 minutes to 1 hour, preferably about 10 minutes followed by a temperature of about 0°-30° C., preferably about 25° C., for about 5 minutes to 1 hour, preferably about 10 minutes. When the reaction is substantially complete, the mixed anhydride (3') is isolated by conventional means. The mixed anhydride (3') is hygroscopic and unstable to heat and moisture, and is therefore preferably used in the next step without delay.

Step (c)

In Step (c), the mixed anhydride (3') is converted to a ketone of formula (6'). Typically, compound (3') is dissolved in an inert solvent as defined above, preferably tetrahydrofuran, and cooled to a temperature of about −100° C. to −50° C., preferably about −60° C. to −70° C. To the cooled solution is added 1-2 molar equivalents, preferably about 1.1 molar equivalents, of a Grignard reagent (5'), formed from commercially available 4-bromoveratrole, at such a rate that the temperature is maintained within the preferred range. The reaction mixture is then allowed to rise to a temperature of about 0°-30° C., preferably about 25° C., for about 5-30 hours, preferably about 14 hours. When the reaction is substantially complete, the (R)-2-(3,4-dimethoxybenzoyl)-1-trifluoroacetylpyrrolidine (6') is isolated and purified by conventional means, preferably chromatography.

Step (d)

In Step (d), the benzoylpyrrolidine (6') is reduced to the corresponding benzylpyrrolidine (7'). Typically, compound (6') is dissolved in an inert solvent as defined above, preferably methylene chloride. To the solution is added from 5 to 20 molar equivalents, preferably about 11 molar equivalents, of a reducing agent, preferably triethylsilane/boron trifluoride etherate mixture. The reaction is carried out at a temperature of about 0°-30° C., preferably about 25° C., for about 1-7 days, preferably about 3 days. When the reaction is substantially complete, the benzylpyrrolidine (7') is isolated by conventional means.

Step (e)

In Step (e), the amine protecting group is removed from the benzylpyrrolidine (7'). Typically, compound (7') is dissolved in a protic solvent such as ethanol, n-propanol, n-butanol, t-butanol and the like, preferably isopropanol, and to the solution is added from 5-50 molar equivalents, preferably about 20 molar equivalents, of an acid, for example sulfuric acid, HBr and the like, preferably 12.5M hydrochloric acid. The reaction is carried out at the reflux temperature of the solvent chosen, preferably about 70°-90° C., for about 8-48 hours, preferably about 24 hours. When the reaction is substantially complete, the (R)-2-(3,4-dimethoxybenzyl)-pyrrolidine (8') is isolated by conventional means.

It should be noted at this point that substituted 2-benzylpyrrolidines, and their preparation, are disclosed in U.S. Pat. No. 4,297,918 (Eistetier et al.), and references cited therein. Further, a convenient synthesis of 2-(3,4-dimethoxybenzyl)pyrrolidine is disclosed in U.S. patent application Ser. No. 07/633,636, filed Dec. 21, 1990, entitled "Process for Preparing Cyclic Amines".

Step (f)

In Step (f), two equivalents of compound (8') are reacted with one equivalent of a bis(acid chloride) to give the diketone (10'). The alkylene linking group of the bis(acid chloride) can contain from 1 to 8, preferably 2 to 6, and more preferably 4 carbon atoms. Typically, compound (8') is dissolved in an inert solvent as defined above, preferably methylene chloride, and to the solution is added from 0.5-0.9 molar equivalents, preferably about 0.67 molar equivalents, of a bis(acid chloride) of formula ClC(O)(CH$_2$)$_p$C(O)Cl, in which p is equal to m-2. The mixture is cooled to a temperature of about −20° C. to 10° C., preferably about 0° C. To the cooled solution is added from 1–10 molar equivalents, preferably about 3 molar equivalents, of a tertiary organic base, such as pyridine, N-methylpiperidine and the like, preferably triethylamine. The temperature of the reaction mixture is then allowed to rise to a temperature of about 0°–30° C., preferably about 25° C., for about 30 minutes to 4 hours, preferably about 1 hour. When the reaction is substantially complete, the diketone (10') is isolated by conventional means.

Step (g)

In Step (g), the diketone (10') is reduced to the bis(-benzylpyrrolidine) (11'), which is a compound of Formula (I) in which each R$_1$ is methyl. The reduction may be carried out by procedures generally known to those of ordinary skill in the art. For example, a solution of compound (10') in THF is added to a solution containing a five-fold excess of 10M BH$_3$.DMS in THF, under argon, and the mixture heated to reflux for 2 hours, cooled, and anhydrous methanol added dropwise. Saturated HCl-MeOH is added dropwise to decompose excess borane, and the solution heated for 15 minutes. After cooling, the solvent is removed in vacuo, leaving an oily residue, which is dissolved in isopropyl alcohol and ether. The bis(benzylpyrrolidine) (11') crystallizes overnight.

Step (h)

In Step (h), the protecting groups on the phenyl rings are removed, by the same procedure as used in Step 3 of Reaction Scheme I.

It is clear that the racemic compounds of Formula I may also be prepared by the method shown in Reaction Scheme II. However, the preferred method of making mixtures, i.e. racemic and non-racemic mixtures, is as shown in Reaction Scheme I.

Preferred compounds of Formula I are the R,R-stereoisomers; less preferred are the R,S-stereoisomers; and least preferred are the S,S-stereoisomers.

Pharmaceutically acceptable salts of the compounds of Formula I, whether prepared by the methods shown in Reaction Scheme I, Reaction Scheme II, or otherwise, are prepared by reacting a free base of Formula I with an appropriate acid. Free bases of Formula I are prepared by reacting a salt of a compound of Formula I with an appropriate base. Esters of compounds of Formula I are prepared by reacting a compound of Formula I with acids or, preferably, acyl halides such as acyl chlorides of the formula R$_3$C(O)Cl or carbamoyl chlorides of the formula R$_3$R$_4$NC(O)Cl. Such acyl chlorides and carbamoyl chlorides are well-known and generally commercially available. Techniques for the preparation of pharmaceutically acceptable salts of amine bases such as the compounds of Formula I, for the interconversion of salts, for the preparation of free bases from salts, and for the preparation of esters, are well-known to the art of pharmaceutical organic synthesis; and those of ordinary skill in the art will have no difficulty, having regard to their knowledge and this disclosure, in performing such reactions.

UTILITY AND ADMINISTRATION

The compounds of Formula I, and the pharmaceutically acceptable esters and salts thereof, are useful in the treatment of hypertension and congestive heart failure in mammals. These compounds can be used both prophylactically and therapeutically.

Pharmaceutical dosage forms which include compositions containing compounds of Formula I and salts or esters thereof are thus administered to patients suffering from hypertension or congestive heart failure. The compounds act to relieve blood pressure and improve heart action by acting as dopamine agonists. In addition, these compositions may be used to treat other conditions as recognized by those of ordinary skill in the art.

Compounds of the present invention can be used to prepare pharmaceutical compositions, useful in the treatment of hypertension and congestive heart failure in mammals, comprising a therapeutically effective amount of a compound of Formula I, or a pharmaceutically acceptable salt or ester thereof, in admixture with a pharmaceutically acceptable carrier. A therapeutically effective amount is that amount which, when administered to a mammal in need thereof, is sufficient to effect treatment, as defined above. Thus, the level of the drug in the formulation can vary from about 1 percent weight (% w) to about 99% w of the drug based on the total formulation and about 1% w to 99% w excipient.

The compounds of the invention can be administered by any suitable means but are usually administered by I.V. or orally: oral administration is most preferred. The R,R-stereoisomer is given orally in an amount of 0.1–500 mg per kilogram of body weight, preferably 3–30 mg per kilogram of body weight. The amount can be adjusted over a wide range depending on the needs and condition of the mammal.

Useful pharmaceutical carriers for the preparation of the pharmaceutical compositions hereof can be solids or liquids. Thus, the compositions can take the form of tablets, pills, capsules, powders, sustained release formulations, solutions, suspensions, elixirs, aerosols, and the like. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical carriers and their formulations are described in "*Remington's Pharmaceutical Sciences*" by E. W. Martin.

One aspect of this invention is a method for treating congestive heart failure or hypertension in a mammali (particularly a human), which comprises administering a therapeutically effective amount of a compound of Formula I, or a pharmaceutically acceptable salt or ester thereof, to a mammal in need thereof.

In the practice of the above described method of this invention, a therapeutically effective amount of the compound of Formula I or a pharmaceutical composition containing it is administered via any of the usual and acceptable methods known in the art, either singly or in combination with another compound or compounds of the present invention or other pharmaceutical agents. These compounds or compositions can thus be administered orally, systemically (e.g., transdermally, intranasally or by suppository) or parenterally (e.g., intramuscularly, subcutaneously and intravenously), and can be administered either in the form of solid or liquid dosages including tablets, solutions, suspensions, aerosols, and the like, as discussed in more detail above.

The formulation can be administered in a single unit dosage form for continuous treatment or in a single unit dosage form ad libitum when relief of symptoms is specifically required.

EXAMPLES

The following examples are put forth so as to provide those of ordinary skill in the art with a complete disclosure and description of compounds and compositions of the invention, how to carry out the processes and use the compounds and compositions of the invention, and are not intended to limit the invention. Unless indicated otherwise, parts are parts by weight, temperature is in ° C. and is at room temperature (20° C. to 30° ), and pressure is at or near atmospheric.

REACTION SCHEME I

Step 1

1,6-Bis[2-(3,4-dimethoxybenzyl)pyrrol-1-yl]hexane

A solution of 2-(3,4-dimethoxybenzyl)pyrrole (2.5 g, 11.5 mmol) in dry DMF (40 mL) was added to a stirred suspension of 50% sodium hydride dispersed in mineral oil (0.663 g, 13.8 mmol) in dry DMF (5 mL) at room temperature, under a nitrogen atmosphere. After 2 hours, 1,6-dibromohexane (1.24 g, 5.7 mmol) was added dropwise, during which time the reaction temperature rose to about 50° C. The solution was stirred for 3 hours at room temperature, by which time the reaction was complete as judged by TLC {hexane-ethyl acetate (4:2)}. The solution was poured into an ice-water mixture and the product extracted into ethyl acetate (3×100 mL). The extract was washed with saturated sodium chloride solution (5×100 mL), dried over sodium sulfate and evaporated in vacuo. The residue was subjected to column chromatographic purification on silica gel (150 g); the product being eluted with the solvent system mentioned above. Recrystallization from dichloromethane-hexane gave 1,6-bis[2-(3,4-dimethoxybenzyl)pyrrol-1-yl]hexane as a crystalline solid.

Step 2

1,6-Bis[2-(3,4-dimethoxybenzyl)pyrrolidin-1-yl]hexane

A solution of 1,6-bis[2-(3,4-dimethoxybenzyl)-pyrrol-1-yl]hexane (2.5 g) in glacial acetic acid (30 mL) containing suspended 5% rhodium on alumina catalyst (1.87 g) was reduced at room temperature and an initial hydrogen pressure of 45 p.s.i.g. (3 hour reaction, followed by TLC). The mixture was filtered through Celite. The filtrate was dried at reduced pressure, and the residue dissolved in dichloromethane, washed with ammonium hydroxide solution and dried over sodium sulfate. The solvent was removed in vacuo, and the residue subjected to column chromatographic purification on silica gel (100 g) using dichloromethane, to elute 1,6-bis[2-(3,4-dimethoxybenzyl)pyrrolidin-1-yl]hexane, 2.5 g (92% yield) as an oil.

Step 3

1,6-Bis[2-(3,4-dihydroxybenzyl)pyrrolidin-1-yl]hexane 1,6-bis[2-(3,4-dimethoxybenzyl)pyrrolidin-1-yl]hexane was dissolved in dry $CH_2Cl_2$ and cooled to −70° C. under inert atmosphere. $BBr_3$ was added. The mixture was warmed to room temperature and $CH_3OH$ was added. The solvent was removed in vacuo to give 1,6-bis-[2-(3,4-dihydroxybenzyl)pyrrolidin-1-yl]hexane.

Step 3A 1,6-Bis[2-(3,4-dihydroxybenzyl)pyrrolidin-1-yl]hexane dihydrobromide A solution of 1,6-bis[2-(3,4-dimethoxybenzyl)-pyrrolidin-1-yl]hexane (2.2 g, 4.4 mmol), from Step 2, was heated in 48% hydrobromic acid (11 mL) at reflux temperature for 3 hours (the reaction was followed by TLC on silica gel). The solution was cooled to room temperature; and the aqueous phase was decanted from the oil, which separated from solution. Toluene was added to this oil and then removed in vacuo. This addition and removal of toluene was repeated several times to remove water and hydrogen bromide. The residual solid, 1,6-bis[2-(3,4-dihydroxybenzyl)pyrrolidin-1-yl]hexane dihydrobromide, a mixture of the R,R—; S,S—; and R,S-stereoisomers, was obtained as a foam.

In a similar manner, using the appropriate ZXZ compound, such as another dibromoalkane, and following steps 1 through 3 above, the following compounds can be obtained:

(±)-1,2-bis[2-(3,4-dihydroxybenzyl)pyrrolidin-1-yl]-ethane;

(±)-1,3-bis[2-(3,4-dihydroxybenzyl)pyrrolidin-1-yl]-propane;

(±)-1,4-bis[2-(3,4-dihydroxybenzyl)pyrrolidin-1-yl]-butane;

(±)-1,5-bis[2-(3,4-dihydroxybenzyl)pyrrolidin-1-yl]-pentane;

(±)-1,7-bis[2-(3,4-dihydroxybenzyl)pyrrolidin-1-yl]-heptane;

(±)-1,8-bis[2-(3,4-dihydroxybenzyl)pyrrolidin-1-yl]-octane;

(±)-1,9-bis[2-(3,4-dihydroxybenzyl)pyrrolidin-1-yl]-nonane; and (±)-1,10-bis[2-(3,4-dihydroxybenzyl)pyrrolidin-1-yl]-decane.

Further, using other ZXZ compounds such as bis(2-chloroethyl) ether, or bis(2-methanesulfonyloxyethyl) ether, which may be prepared from bis(2-hydroxyethyl) ether, and following Steps 1 through 3 above, there may be prepared compounds such as (±)-1,5-bis[2-(3,4-dihydroxybenzyl)pyrrolidin-1-yl]-3-oxapentane; and other compounds in which Z is —$(CH_2)_n Y(CH_2)_n$—and Y is O or S.

REACTION SCHEME II

STEP (a)

(R)-1-trifluoroacetylproline (R)-proline (20 g, 0.174 mol) was placed in a 500 mL round-bottom flask. To this was added 100 mL THF and ethyl trifluoroacetate (50 g, 0.34 mol). The solution was purged with argon and 1,1,3,3-tetramethylguanidine (30 g, 0.261 mol) was added dropwise. The solution was allowed to stir until all the (R)-proline had dissolved (approximately 35 minutes). The solvent was removed in vacuo and the residue dissolved in $CH_2Cl_2$ (200 mL). The solution was washed with 6N HCl (aqueous, 2×100 mL). The organic layer was separated and dried with $Na_2SO_4$, filtered and the solvent removed in vacuo to give as an oil which crystallized upon standing; yield 29 g (79%), m.p. 48°–51° C.

Step (b)

(R)-1-trifluoroacetylproline anhydride with diphenylphosphoric acid (R)-1-trifluoroacetylproline (29 g, 0.137 mol) was dissolved in $CH_2Cl_2$ (300 mL) in a 1 liter round-bottom flask and cooled to 0° C. To this solution was added diphenyl chlorophosphate (36.9 g, 0.137 mol) followed by 4-methylmorpholine (15.27 g, 0.151 mol). After stirring at 0° C. for 10 minutes, the reaction mixture was allowed to warm to room temperature and stirred for an additional 10 minutes. The solution was then diluted with 600 mL dry diethyl ether. After filtration, the filtrate was washed with a saturated aqueous solution of $NaHCO_3$; and then the organic layer was separated, dried with $MgSO_4$, filtered, and the solvent removed in vacuo to give 54.8 g (R)-1-trifluoroacetylproline anhydride with diphenylphosphoric acid (90% yield), as a solid which was hygroscopic and unstable to heat and moisture.

Step (c)

(R)-2-(3,4-dimethoxybenzoyl)-1-trifluoroacetylpyrrolidine

To a 250 mL round-bottom flask was added magnesium turnings (4.51 g, 0.186 mol) and 100 mL dry THF. Iodine (one crystal) was added, followed by 4-bromoveratrole (27 g, 0.124 mol) dropwise. The reaction was heated under reflux after addition of the first few drops of 4-bromoveratrole until the iodine color disappeared. Following this, the remainder of the 4-bromoveratrole was added dropwise. A condition of reflux was maintained for 2 hours. The solution was then cooled to room temperature and added to a solution of (R)-1-trifluoroacetylproline anhydride with diphenylphosphoric acid (54 g, 0.123 mol) in 250 mL dry THF at $-70°$ C. The rate of addition was monitored to keep the reaction temperature below $-60°$ C. Once addition was complete, the reaction mixture was warmed to room temperature and allowed to stir for 14 hours. It was then poured into a saturated aqueous solution of ammonium chloride (500 mL) and shaken. The organic layer was separated, dried with $MgSO_4$, and filtered, and the solvent removed in vacuo to give an oil. This oil was subjected to flash chromatography in 1:1 hexane:ethyl acetate to give 20.4 g of (R)-2-(3,4-dimethoxybenzoyl)-1-trifluoroacetyl-pyrrolidine (50% yield), m.p. 121°–123° C., $[\alpha]_D^{25} = 65°$ (c=1.2, $CHCl_3$).

Step (d)

(R)-2-(3,4-dimethoxybenzyl)-1-trifluoroacetylpyrrolidine (R)-2-(3,4-dimethoxybenzoyl)-1-trifluoroacetylpyrrolidine (4.9 g, 0.015 mol) was dissolved in 50 mL dry $CH_2Cl_2$ in a 500 mL round-bottom flask. To the solution was added triethylsilane (20 g, 0.172 mol) and $BF_3 \cdot Et_2O$ (50 mL). The reaction mixture was stirred at room temperature for 3 days, after which time a saturated aqueous solution of potassium carbonate was added cautiously in a dropwise manner. When no more gas was evolved, 100 mL $CH_2Cl_2$ was added. The mixture was then shaken. The triphasic mixture was filtered through a glass fritted funnel, and the organic layer separated and dried with $MgSO_4$. Removal of the solvent in vacuo yielded 3.2 g of (R)-2-(3,4-dimethoxybenzyl)-1-trifluoroacetylpyrrolidine (68% yield), as an oil which could be used without further purification.

Step (e)

(R)-2-(3,4-dimethoxybenzyl)pyrrolidine

To a solution of (R)-2-(3,4-dimethoxybenzyl)-1-trifluoroacetylpyrrolidine (3.2 g, 0.010 mol) in 50 mL isopropyl alcohol was added 15 mL of 12.5M HCl. The mixture was then heated under reflux until all starting material had disappeared, approximately 24 hours. The solvent was removed in vacuo to give an oil which could be recrystallized from isopropyl alcohol/ether, giving 2.5 of (R)-2-(3,4-dimethoxybenzyl)pyrrolidine (97% yield), as needles, m.p. 165°–167° C.

Step (f)

(R,R)-1,6-bis[2-(3,4-dimethoxybenzyl)-pyrrolidin-1-yl]-1,6-dioxohexane

To a 100 mL round-bottom flask was added (R)-2-(3,4-dimethoxybenzyl)pyrrolidine (0.75 g, (0.003 mol), 35 mL $CH_2Cl_2$, and adipoyl chloride (0.002 mol). The solution was cooled to 0° C., and triethylamine (0.911 g, 0.009 mol) was added. The solution immediately clouded, and was warmed to room temperature. After 1 hour at room temperature, the mixture was poured into 1N HCl (35 mL), and shaken. The organic layer was separated, dried with $Na_2SO_4$, filtered, and the solvent removed in vacuo to give (R,R)-1,6-bis[2-(3,4-dimethoxybenzyl)pyrrolidin-1-yl]-1,6-dioxohexane as an oil, which was purified via column chromatography on silica with 5% methanol in methylene chloride.

Step (g)

(R,R)-1,6-bis[2-(3,4-dimethoxybenzyl)-pyrrolidin-1-yl]hexane (R,R)-1,6-bis[2-(3,4-dimethoxybenzyl)pyrrolidin-1-yl]-1,6-dioxohexane (0.001 mol) in dry THF was added to a solution containing 0.5 mL (0.005 mol) 10M $BH_3 \cdot DMS$, and the solution was heated under reflux in an argon atmosphere. Heating was maintained for 2 hours, after which time the mixture was cooled and 10 mL anhydrous methanol was added dropwise. After gas evolution had subsided, 10 mL of saturated HCL-MeOH was added dropwise and the mixture heated under reflux for 15 minutes. The mixture was cooled to room temperature and the solvent removed in vacuo, leaving an oily residue whose volume was further reduced by Kugelrohr distillation (100° C., 0.05 Torr). Finally, the residue was dissolved in isopropyl alcohol, and ether was added until the solution became cloudy. Crystallization occurred overnight, giving (R,R)-1,6-bis[2-(3,4-dimethoxybenzyl)pyrrolidin-1-yl]hexane.

Step (h)

(R,R)-1,6-bis[2-(3,4-dihydroxybenzyl)-pyrrolidin-1-yl]hexane

To a solution of (R,R)-1,6-bis-[2-(3,4-dimethoxy-benzyl)pyrrolidin-1-yl]hexane (0.001 mol) in dry $CH_2Cl_2$ at $-70°$ C. under an inert atmosphere was added $BBr_3$ (4 mL of a 1M solution, 0.004 mol). The reaction mixture was warmed to room temperature, recooled to $-70°$ C., and $CH_3OH$ (4 mL) was added. After warming to room temperature, the solvent was removed in vacuo. The residue was subjected to column chromatography, eluting with $CH_3OH$. The fractions containing the desired product were concentrated in vacuo to provide (R,R)-

1,6-bis[2-(3,4-dihydroxybenzyl)pyrrolidin-1-yl]-hexane, $[\alpha]_D^{25} = 12.86°$.

By following Steps (f), (g) and (h), starting with the appropriate optically pure (R)- or (S)-proline derivative and the appropriate $ClC(O)(CH_2)_pC(O)Cl$ in which p is equal to m-2, where m is as defined above, for example p=2, 3, 5, 6, 7 or 8, one obtains the following compounds:

(R,R)-1,4-bis[2-(3,4-dihydroxybenzyl)pyrrolidin1-yl]butane;
(S,S)-1,4-bis[2-(3,4-dihydroxybenzyl)pyrrolidin1-yl]butane;
(R,R)-1,5-bis[2-(3,4-dihydroxybenzyl)pyrrolidin1-yl]pentane;
(S,S)-1,6-bis[2-(3,4-dihydroxybenzyl)pyrrolidin1yl]hexane;
(R,R)-1,7-bis[2-(3,4-dihydroxybenzyl)pyrrolidin1-yl]heptane;
(S,S)-1,7-bis[2-(3,4-dihydroxybenzyl)pyrrolidin1-yl]heptane;
(R,R)-1,8-bis[2-(3,4-dihydroxybenzyl)pyrrolidiin1-yl]octane; and
(S,S)-1,8-bis[2-(3,4-dihydroxybenzyl)pyrrolidin1-yl]octane.

Further, by following Steps (f), (g) and (h), starting with a mixture of (R)- and (S)-proline derivatives and/or derivatives where $R_2$ is not hydrogen and/or bis(acid chlorides) of the formula $ClC(O)(CH_2)_{n-1}Y(CH_2)_n$-$C(O)Cl$ whe obtains mixtures of isomers of compounds of Formula I, compounds of Formula I in which $R_2$ is not hydrogen, compounds of Formula I in which X is $-(CH_2)_nY(CH_2)_n-$, and compounds of Formula I in which more than one of these variations exists.

DATA

A. Goldberg Renal and Femoral In Vivo Dog Model

The compounds were subsequently tested following intra-arterial administration in an in situ renal and femoral arterial preparation in the dog, as developed by L. I. Goldberg, to test for DA1 and DA2 dopamine activity, respectively. Details of the methodology are provided in the *European J. Pharmacol., 89:137, 1983*, as well as in *Hypertension*, 6:1-25, 1984. These compounds were found to be highly active when compared to dopamine and di-propyldopamine, the respective DA1 and DA2 standards for this preparation.

The test compound (R,R)-1,6-bis[2-(3,4-dihydroxybenzyl)pyrrolidin-1-yl]hexane was tested in the Goldberg renal and femoral dog assays for $DA_1$ and $DA_2$ activity. In contrast to our $DA_2$ standard agent, the activity of some of these compounds has been difficult to characterize in the Goldberg femoral assay. This entire series of compounds, however, displays highly potent and specific $DA_1$ activity.

The compound was injected directly into the renal or femoral artery for analysis of $DA_1$ or $DA_2$ activity, respectively. Since the compound was introduced into the $DA_1$ and $DA_2$ receptor beds in minimal doses, specific renal and femoral vasodilation was observed in the absence of systemic effects. The compound was tested for relative activity in comparison to the standard $DA_1$ agonist, dopamine or the standard $DA_2$ agonist, DPDA. Specific $DA_1$ or $DA_2$ activity of the tested compound was verified by SCH 23390 or domperidone blockade.

Adult mongrel dogs of either sex (11-20 kg) were anesthetized with pentobarbital sodium (33 mg/Kg, i.v.). the animals were intubated and ventilated with room air using a Harvard respirator.

Renal

The abdominal aorta was catheterized with a Millar micro-tip (size 5F) transducer via the right femoral artery for pressure monitoring. The right femoral vein was cannulated with PE-160 tubing for iv saline infusion, as well as, supplemental pentobarbital administration. The left renal artery was isolated through a lateral abdominal incision. An electromagnetic flowprobe of the appropriate size (9-12 mm circ) was placed around the artery and connected to a Carolina Medical electromagnetic flowmeter. Surface ECG leads were placed subcutaneously on the chest and limbs to monitor heart rate. A 25 gauge ⅜" needle bent 90°, 4 mm from the tip, was placed in the renal artery proximal to the probe and connected to an infusion pump delivering saline at a constant rate of 1 mL/min. Following a saline and norepinephrine (NE), 5.92 nmol, challenge, given in an injection volume of 0.2 mL, the animal was treated with a phenoxybenzamine, 0.5 mg/Kg/min i.a., infusion for a duration of 10-20 minutes as necessary to achieve a complete blockade of the NE challenge. Blood pressure was maintained by supplemental saline (10-20 mL/Kg, iv). Bradykinin, a standard for nonspecific vasodilation, was given at 0.62 nmol doses, in 0.2 mL saline, i.a., prior to generating a dose response curve for dopamine in which 4-fold increase doses, ranging from 3 to 48 nmol, were injected i.a. in 0.2 mL of saline. The test compound was injected similarly in 4-fold increasing doses up to a maximum of 3000 nmol. Dosing of the test compound was then repeated following SCH 23390 pretreatment (0.05-0.10 mg/Kg, i.v.).

Femoral

The thoracic aorta was catheterized with a Millar micro-tip (size 5F) transducer via the right carotid artery for pressure monitoring. The right external jugular vein was cannulated with PE-160 tubing for supplemental pentobarbital administration. The left femoral artery was isolated and an electromagnetic flowprobe of the appropriate size (8-12 mm circ) was placed around the artery and connected to a Caroline Medical electromagnetic flowmenter. Surface ECG leads were placed subcutaneously on the chest and limbs to monitor heart rate. A 25 gauge ⅜" needle bent 90°, 4 mm from the tip, was placed in the femoral artery proximal to the probe and connected to an infusion pump delivering saline at a constant rate of 1 mL/min. Following a saline and bradykinin challenge (0.02 or 0.04 nmol, in 0.2 mL saline, i.a.), a dose response curve for DPDA was generated by injecting 4-fold increasing doses ranging from 3 to 190 nmol in 0.2 mL of saline. The test compound was injected similarly in 4-fold increasing doses up to 3000 nmol. Dosing of the test compound was then repeated following domperidone pretreatment (10-60 mcg/Kg, i.v.).

Data Analysis

The optimal dose of compound was defined as that which produced a maximum increase in blood flow before causing a change in systemic blood pressure. Efficacy ratios were determined by division of the optimal response of the test compound by the optimal response of the standard agent. $ED_{50}$ values were derived by regression analysis from individually generated dose response curves. Potency ratios were the quotients calculated from the division of the standard agent $ED_{50}$ by the $ED_{50}$ of the test compound. This data together with the information on the percent blockade of optimal doses of the active compounds following antagonist administration is present in the following Table. If the inhibition of the test compound was similar to that of dopamine or DPDA, the compound was considered to be a $DA_1$ or $DA_2$ agonist, respectively.

| Compound | N | $ED_{50}$ (nmol) | Relative Potency to $DA_1$ Standard | Relative Efficacy to $DA_1$ Standard | Percent Block Following SCH 23390 |
|---|---|---|---|---|---|
| RENAL $DA_1$ ASSAY | | | | | |
| Standard: | | | | | |
| Dopamine | 12 | | 1.00 | 1.00 | 100% |
| Test Compound | 3 | 0.63 | 11.71 | 1.05 | 100% |

| Compound | N | $ED_{50}$ (nmol) | Relative Potency to $DA_2$ Standard | Relative Efficacy to $DA_2$ Standard | Percent Block Following Domperidone |
|---|---|---|---|---|---|
| RENAL $DA_2$ ASSAY | | | | | |
| Standard: | | | | | |
| DPDA | 21 | | 1.00 | 1.00 | 100% |
| Test Compound | 1 | 0.19 | 58.63 | 0.60 | 60% |
| Test Compound | 2 | | slight local constriction | | |

B. Spontaneous Hypertensive Rat—Diuretic Activity

Additionally, these compounds were examined for diuretic activity for 6 hours following oral administration in the saline-loaded spontaneously hypertensive rat (SHR). Methods for this assay have been previously described (Rosenkranz, et al, *Proc. West. Pharmacol. Soc.* 28:87, 1985). The diuretic and natriuretic effects elicited by these compounds were characterized by an immediate onset of action. Over the course of the 6 hour study, these compounds were found to be as efficacious as the standard diuretic agent, hydrochlorothiazide.

Male spontaneously hypertensive SHR/NCrlBR rats weighing 320–430 gms were divided into four groups of seven animals. All animals were food- and water-deprived overnight. The following morning, each group of rats was hydrated with deionized water (20 mL/Kg, po) forty-five minutes prior to the administration of vehicle or the test compound (R,R)-1,6-bis[2-(3,4-dihydroxybenzyl)-pyrrolidin-1-yl]hexane.

Following vehicle or drug, the rats were placed in individual metabolic units. Fifteen minutes post-dose the animals were saline-loaded (30 mL/Kg, po). Urine was collected at 1, 3 and 6 hour intervals post-saline-load. Urine volumes were measured and sodium and potassium levels were determined by flame photometry.

A two-way analysis of variance with time, treatment and their interaction was run as a repeated measures analysis. A secondary model of one-way analysis of variance (by time) was run using specified contrasts. The p-values for the contrasts were adjusted using Fisher's LSD strategy at each time point.

One hour post oral administration of the test compound at 10 mg/Kg, significant diuresis and natriuresis were observed. diuresis and natriuresis (p<0.05) were observed at the 30 mg/Kg dose level at 1, 3 and 6 hours post-dose. Administration of 30 mg/Kg, po, produced significant kaliuresis at the 1 and 3 hour post-dose time points. The lowest dose (3 mg/Kg, po) elicited significant urine and sodium retention at 1 hour and 1 and 3 hours, respectively.

THE EFFECTS ON URINE VOLUME, SODIUM AND POTASSIUM EXCRETION IN THE SPONTANEOUSLY HYPERTENSIVE RAT

| Cumulative Time (hr) | Control Vehicle[b] | Test Compound 3 mg/Kg, po | Test Compound 10 mg/Kg, po | Test Compound 30 mg/Kg, po |
|---|---|---|---|---|
| | | Urine Volume (mL) $X \pm S.D., N = 7$ | | |
| 1 | 5.5 ± 1.0 | 2.8 ± 1.0* | 7.6 ± 1.3* | 13.9 ± 2.0* |
| 3 | 8.6 ± 0.9 | 7.5 ± 1.5 | 10.1 ± 3.2 | 22.4 ± 1.8* |
| 6 | 9.6 ± 0.8 | 9.4 ± 2.3 | 11.0 ± 3.2 | 22.8 ± 1.8* |
| | | Urine $Na^+$ (mEq/sample) $X \pm S.D., N = 7$ | | |
| 1 | 0.01 ± 0.01 | 0.00 ± 0.00* | 0.03 ± 0.01* | 0.21 ± 0.10* |
| 3 | 0.09 ± 0.06 | 0.03 ± 0.05* | 0.13 ± 0.07 | 0.62 ± 0.20* |
| 6 | 0.17 ± 0.11 | 0.16 ± 0.13 | 0.22 ± 0.10 | 0.73 ± 0.19* |
| | | Urine $K^+$ (mEq/sample) $X \pm S.D., N = 7$ | | |
| 1 | 0.04 ± 0.01 | 0.02 ± 0.01 | 0.04 ± 0.01 | 0.08 ± 0.04* |
| 3 | 0.11 ± 0.03 | 0.08 ± 0.03 | 0.11 ± 0.05 | 0.20 ± 0.09* |
| 6 | 0.17 ± 0.06 | 0.17 ± 0.05 | 0.18 ± 0.07 | 0.25 ± 0.09 |

*$p < 0.05$ as compared to control (SAS statistical analysis program).
[b]2% ethanol and 0.5% Tween in deionized water.

C. Spontaneous Hypertensive Rats—Antihypertensive Activity

The compounds of this invention were screened for oral antihypertensive activity in the conscious restrained rat. Adult male SHR were instrumented for blood pressure and heart rate measurements under light ether anesthesia. The animals were maintained on a plexiglass restraining board following surgery, and were allowed a 1 hour recovery period prior to the oral administration of the test compounds. These compounds were found to decrease blood pressure in the absence of a reflex tachycardia for up to 4 hours post-dosing.

Male spontaneously hypertensive rats, SHR/NVrl Br (320–410 g) were fasted overnight. The following morning the left femoral artery and vein of each rat was cannulated under light ether anesthesia. following surgery, the rats were placed on a rat restraining board and allowed to recover from the effects of the ether for 1 hour. ECG leads were placed on the animal's chest to monitor heart reate. Animals were divided into groups of 4 and dosed with the test compound (R,R)-1,6-bis[2-(3,4-dihydroxybenzyl)pyrrolidin-1-yl]-hexane.

Blood pressure and heart rate readings were taken at 5 minute intervals for the first 15 minutes and every 15 minutes thereafter for a duration of 4 hour post-compound administration. Data was evaluated by two-tailed paired t-tests.

The test compound (3, 10 and 30 mg/Kg, po) elicited a significant decrease in mean blood pressure. Peak decreases ranged from −17 to −22% while duration of action lasted between 15–210 minutes. The heart rate was significantly increased following administration of the test compound 3 mg/Kg, po, (6% for 90 minutes). Conversely, 10 mg/Kg, po, decreased (p<0.05) the heart rate for 1 hour post-compound administration (max. response of −14%). 30 mg/Kg, po, did not elicit any biologically significant changes in heart rate.

D. Toxicity

Rats were administered (R,R)-1,6-bis[2-(3,4-dihydroxybenzyl)pyrrolidin-1-yl]-hexane in doses of 30 and 100 mg/Kg once a day for 7 days. All rats survived for the duration of the treatment. No treatment related changes were noted in clinical condition, body weight, or food intake.

What is claimed is:

1. A compound of Formula I

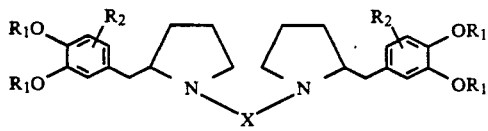

in which:

$R_1$ is hydrogen, —C(O)$R_3$, or —C(O)N$R_3R_4$, where $R_3$ and $R_4$ are independently lower alkyl, phenyl, or phenyl lower alkyl;

$R_2$ is hydrogen or lower alkyl; and

X is —(CH$_2$)$_m$— where m is an integer of 1 to 10, or —(CH$_2$)$_n$Y(CH$_2$)$_n$— where n is an integer of 1 to 3 and Y is oxygen or sulfur, as an individual R,R—; R,S—; or S,S-stereoisomer, or a racemic or non-racemic mixture of stereoisomers, or a pharmaceutically acceptable salt of an individual R,R—; R,S—; or S,S-stereoisomer, or of a racemic or non-racemic mixture of stereoisomers.

2. The compound of claim 1 wherein $R_1$ and $R_2$ are hydrogen, as an individual R,R—; R,S—; or S,S-stereoisomer, or a racemic or non-racemic mixture of stereoisomers, or a pharmaceutically acceptable salt of an individual R,R—; R,S—; or S,S-stereoisomer, or of a racemic or non-racemic mixture of stereoisomers.

3. The compound of claim 2 wherein X is —(CH$_2$)$_m$— and m is an integer from 4 to 8, as an individual R,R—; R,S—; or S,S-stereoisomer, or a racemic or non-racemic mixture of stereoisomers, or a pharmaceutically acceptable salt of an individual R,R—; R,S—; or S,S-stereoisomer, or of a racemic or non-racemic mixture of stereoisomers.

4. The optically pure R,R-stereoisomer of the compound of claim 3, or a pharmaceutically acceptable salt thereof.

5. The compound of claim 4 wherein m is 6, namely (R,R)-1,6-bis-[2-(3,4-dihydroxybenzyl)pyrrolidin-1-yl ]-hexane, or a pharmaceutically acceptable salt thereof.

6. A pharmaceutically acceptable salt of the compound of claim 5.

7. A pharmaceutical composition, comprising: a pharmaceutically acceptable carrier; and an effective amount of a compound of Formula I

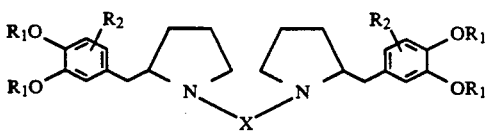

in which:

$R_1$ is hydrogen, —C(O)$R_3$, or —C(O)N$R_3R_4$, where $R_3$ and $R_4$ are independently lower alkyl, phenyl, or phenyl lower alkyl;

$R_2$ is hydrogen or lower alkyl; and

X is —(CH$_2$)$_m$— where m is an integer of 1 to 10, or —(CH$_2$)$_n$Y(CH$_2$)$_n$— where n is an integer of 1 to 3 and Y is oxygen or sulfur, as an individual R,R—; R,S—; or S,S-stereoisomer, or a racemic or non-racemic mixture of stereoisomers, or a pharmaceutically acceptable salt of an individual R,R—; R,S—; or S,S-stereoisomer, or of a racemic or non-racemic mixture of stereoisomers.

8. The composition of claim 7 which comprises the compound of Formula 1 wherein $R_1$ and $R_2$ are hydrogen, as an individual R,R—; R,S—; or S,S-stereoisomer, or a racemic or non-racemic mixture of stereoisomers, or a pharmaceutically acceptable salt of an individual R,R—; R,S—; or S,S-stereoisomer, or of a racemic or non-racemic mixture of stereoisomers.

9. The composition of claim 8 which comprises the compound of Formula 1 wherein X is —(CH$_2$)$_m$— and m is an integer from 4 to 8, as an individual R,R—; R,S—; or S,S-stereoisomer, or a racemic or non-racemic mixture of stereoisomers, or a pharmaceutically acceptable salt of an individual R,R—; R,S—; or S,S-stereoisomer, or of a racemic or non-racemic mixture of stereoisomers.

10. The composition of claim 9 which comprises the optically pure R,R-stereoisomer of the compound of Formula 1, or a pharmaceutically acceptable salt thereof.

11. The composition of claim 10 which comprises the compound of Formula 1 wherein m is 6, namely (R,R)-1,6-bis-[2-(3,4-dihydroxybenzyl)pyrrolidin-1-yl]-hexane, or a pharmaceutically acceptable salt thereof.

12. The composition of claim 11 which comprises a pharmaceutically acceptable salt of (R,R)-1,6-bis-[2-(3,4-dihydroxybenzyl)pyrrolidin-1-yl]-hexane.

13. A compound of Formula I

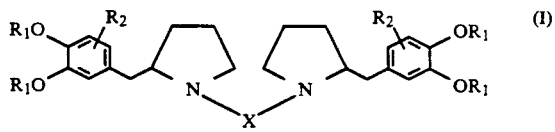

in which:

$R_1$ is lower alkyl;

$R_2$ is hydrogen or lower alkyl; and

X is —(CH$_2$)$_m$— where m is an integer of 1 to 10, or —(CH$_2$)$_n$Y(CH$_2$)$_n$— where n is an integer of 1 to 3 and Y is oxygen or sulfur, as an individual R,R—; R,S—; or S,S-stereoisomer, or a racemic or non-racemic mixture of stereoisomers, or a pharmaceutically acceptable salt of an individual R,R—; R,S—; or S,S-stereoisomer, or of a racemic or non-racemic mixture of stereoisomers.

14. A method of treating hypertension, in a mammal, comprising administering to the mammal in need of treatment a pharmaceutically effective amount of a compound of Formula I

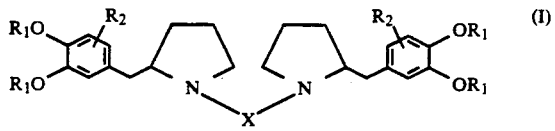

in which:

R$_1$ is hydrogen, —C(O)R$_3$, or —C(O)NR$_3$R$_4$, where R$_3$ and R$_4$ are independently lower alkyl, phenyl, or phenyl lower alkyl;

R$_2$ is hydrogen or lower alkyl; and

X is —(CH$_2$)$_m$— where m is an integer of 1 to 10, or —(CH$_2$)$_n$Y(CH$_2$)$_n$— where n is an integer of 1 to 3 and Y is oxygen or sulfur, as an individual R,R—; R,S—; or S,S—stereoisomer, or a racemic or non-racemic mixture of stereoisomers, or a pharmaceutically acceptable salt of an individual R,R—; R,S—; or S,S—stereoisomer, or of a racemic or non-racemic mixture of stereoisomers, or a pharmaceutically acceptable composition comprising the compound.

15. The method of claim 14 wherein the compound of Formula I is (R,R)-1,6-bis-[2-(3,4-dihydroxybenzyl)pyrrolidin-1-yl]hexane or a pharmaceutically acceptable salt thereof.

* * * * *